(12) United States Patent
Ott

(10) Patent No.: US 7,057,727 B2
(45) Date of Patent: Jun. 6, 2006

(54) DEVICE FOR THE PIXEL-BY-PIXEL PHOTOELECTRIC MEASUREMENT OF A PLANAR MEASURED OBJECT

(75) Inventor: Hans Ott, Regensdorf (CH)

(73) Assignee: Gretag-MacBeth AG, Regensdorf (CH)

( * ) Notice: Subject to any disclaimer, the term of this patent is extended or adjusted under 35 U.S.C. 154(b) by 1047 days.

(21) Appl. No.: 10/004,787

(22) Filed: Dec. 7, 2001

(65) Prior Publication Data

US 2004/0066515 A1  Apr. 8, 2004

(30) Foreign Application Priority Data

Dec. 8, 2000 (EP) .................................. 00126493
Mar. 7, 2001 (EP) .................................. 01105312

(51) Int. Cl.
*G01N 21/25* (2006.01)
(52) U.S. Cl. ...................... 356/418; 356/419; 250/226
(58) Field of Classification Search ................ 356/402, 356/416, 417, 418
See application file for complete search history.

(56) References Cited

U.S. PATENT DOCUMENTS 3,003,388 A * 10/1961 Hunter et al. ............... 356/405
5,008,743 A    4/1991 Katzir et al.
5,724,259 A    3/1998 Seymour et al.

\* cited by examiner

*Primary Examiner*—Gregory J. Toatley, Jr.
*Assistant Examiner*—Roy M. Punnoose
(74) *Attorney, Agent, or Firm*—McCarter & English, LLP

(57) ABSTRACT

The device for the pixel-by-pixel photoelectric measurement of a planar measured object includes projection means for the imaging of the measured object onto a two-dimensional CCD image sensor, filter means provided in the imaging light path for the wavelength selective filtering of the measuring light impinging on the image sensor, signal processing means for the processing of the electrical signals produced by the image sensor and for the conversion thereof into corresponding digital raw measured data, as well as data processing means for the processing of the raw measured data into image data representing the colors of the individual image elements of the measured object. Furthermore, illumination means are provided which include a Fresnel lens, which illuminate the measured object with at least one essentially parallel light bundle under an angle of incidence of essentially 45°+/−5°. The projection means which include at least one tele-lens constructed as a Fresnel lens, are constructed as tele-centrical imaging optics, which image each point of the measured object under essentially the same angle of observation of essentially 0° and with essentially the same aperture angle of essentially maximally 5° onto the light converter element array. The data processing means carry out extensive correction measures.

39 Claims, 10 Drawing Sheets

DEVICE FOR THE PIXEL-BY-PIXEL PHOTOELECTRIC MEASUREMENT OF A PLANAR MEASURED OBJECT

This application claims priority under 35 U.S.C. §§ 119 and/or 365 to 00126493.6 filed in Europe on Dec. 8, 2000, and to 01105312.1 filed in Europe on Mar. 7, 2001; the entire contents of which are hereby incorporated by reference.

FIELD OF THE INVENTION

The invention relates to a device for the pixel-by-pixel photoelectric measurement of a planar or flat measured object or object to be measured.

BACKGROUND ART

So called scanners are used especially in the graphics industry for the pixel-by-pixel photoelectric scanning of planar measured objects. They include a measuring head which is moveable relative to the measured object in one or two dimensions, which captures the spectral remission of respectively one pixel of the measured object or object to be measured by way of a 0/45° measurement geometry and converts it into corresponding electric signals. Scanners equipped with fibre optics are also already known, which can measure a complete image line at once. However, scanners which without relative movement between the measurement head and the measured object can measure a larger measurement surface pixel-by-pixel and with sufficient accuracy for the color measurement and under the for the color measurement generally conventional, standardized geometric conditions and are not known.

On the other hand, video cameras are used for the scanning of images or for recording purposes, which are equipped with a two-dimensional image sensor onto which the complete image to be scanned is projected by way of the camera lens so that no relative movement between the camera and the image is required. The image sensor generally consists of a two-dimensional array of light converter elements integrated into a chip, normally on CCD basis (charge coupled devices). Color enabled video cameras either have several image sensors with upstream color filters or an image converter with integrated color filters. The resolution of the scanning is fixed by the number of light converter elements available for each color channel and by the projection scale.

The geometric conditions for the color measurement are defined by international standards. For the normally used 0/45° measurement geometry the illumination of the measurement surface is to be carried out at 45°+/−5° to the normal of the measurement surface and the remitted measuring light captured at an observation angle of 0°+/−5° to the normal of the measurement surface. The light path can also be selected to be the opposite.

For the color measurement within the image, these measurement conditions must be complied with for each measured point of the measured object. This is not achievable with conventional video cameras under practically realizeable dimensions, since the distances of the light source and the camera from the measured object or object to be measured would have to be much too large.

SUMMARY OF THE INVENTION

A measurement device of the generic type is now to be improved with the present invention such that it is suitable for color measurements.

The solution of the object underlying the present invention is achieved by providing standardized geometrical conditions for each pixel of the measured object.

The standardized geometrical conditions for each pixel of the measured object or object to be measured are achieved by the device in accordance with the invention including a parallel illumination and a tele-centrical projection optics, whereby a conventional video camera with CCD image sensor can be used for the measurement without making the whole arrangement impractically large.

It is especially advantageous when Fresnel lenses are used for generation of the parallel illumination. Furthermore, blend filters can be positioned directly thereon by which a homogenization of the illumination of the measured object can be achieved in a simple manner. It is a further problem of the calorimetric measurement by way of a video camera of large surface measured objects that on the one hand the optical projection means cannot be made completely free of geometrical distortions at reasonable cost and produce more or less pronounced reflection images and that on the other hand scattered or adventitious light effects occur between the individual image points of the measured object and are measured as well because of the necessarily missing measurement shutters or other screening devices. Furthermore, especially with larger measured objects, the angle of incidence of the measurement light on the filters used for the spectral splitting is not the same at all image points, whereby spectral errors occur as well.

It is therefor a further important object of the present invention to provide means for correcting the mentioned interference effects so that the measured data have the precision required for calorimetric applications.

The solution of this further object of the invention is achieved by carrying out corrective measures by way of a data processor. It is especially advantageous when the data processor realizing the corrective measures carries out all desired corrective measures, i.e. a geometry correction, a reflection correction, a scattered light reflection, a white standardization, a white border standardization and a spectral correction.

DETAILED DESCRIPTION OF THE DRAWINGS

Preferred embodiments of the invention will be described in the following by way of example only and with reference to the drawings, wherein.

DETAILED DESCRIPTION OF THE PREFERRED EMBODIMENTS

Figure 1:
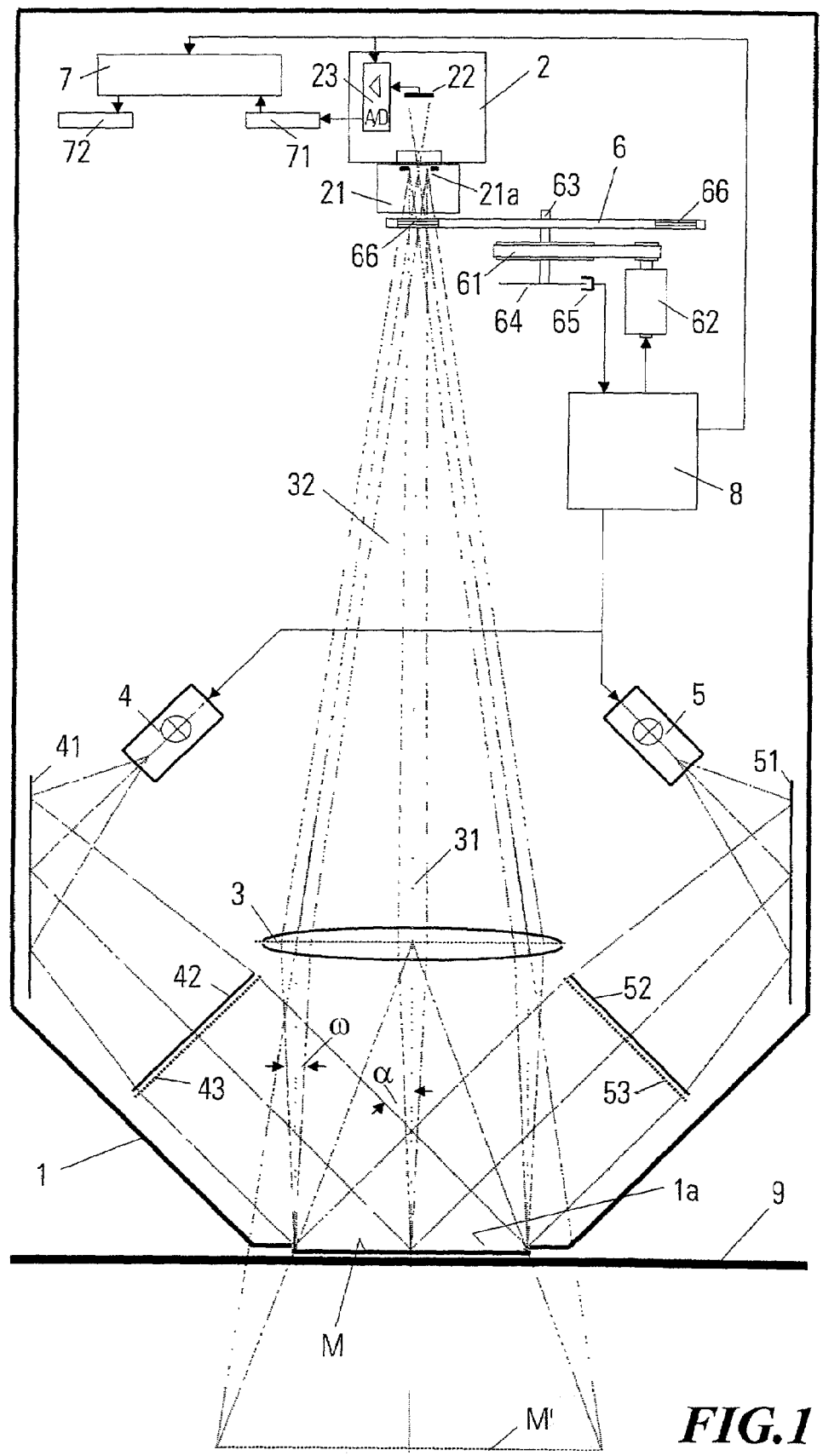
FIG. 1 is a schematic illustration of a first embodiment of the measurement device in accordance with the invention.

The first preferred embodiment of the measurement device in accordance with the invention as schematically illustrated in FIG. 1 includes a light-proof housing 1 with a measurement window 1a, a video camera 2, a tele-lens 3 preferably constructed as a Fresnel lens, two flash light sources 4 and 5, two re-directing mirrors 41 and 51, two illumination lenses 42 and 52 preferably constructed as Fresnel lenses, two blend filters 43 and 53 positioned at the illumination lenses, a filter wheel 6, a belt-drive 61, 62 an angle encoder 64 connected with the axis 63 of the filter wheel 6 and with an associated sensor 65, a data processor 7 and a central process control 8. The data processor 7 and the process control 8 are preferably realized by a digital computer and can of course be positioned outside the housing 1.

The video camera 2 is generally of conventional construction and includes, as parts relevant for the present invention, a standard imaging lens 21, an image sensor 22 in the form of a two-dimensional array of light converter elements, especially so called CCD elements (charge coupled devices) as well as the conventional signal processing electronics 23, which inputs, amplifies and digitalizes the electrical signals produced by the image sensor 22 and makes them available as digital raw measured data 71 at the output of the video camera 2. The image sensor 22 can typically include about 300,000 individual light converter elements with a typical size of about 0.01 mm.

The filter wheel 6 is provided at its circumference with 16 narrow band color filters 66 as well as an infrared transparent window and a non-transparent region. Each color filter 66 is constructed as a bandpass filter and has a bandwidth of 20 nm, and the color filters 66 together cover the visible spectrum of essentially 400–700 nm. The filter wheel is positioned in front of the video camera 2 in such a way that its color filters 66 can be selectively positioned in front of the imaging lens 21 by a corresponding rotation of the filter wheel. The positioning of the color filters 66 is controlled in a generally known manner by the process control 8. The object to be measured M is positioned on a support 9 in front of the measurement window 1a of the housing 1. The tele-lens 3 is positioned between the measurement window 1a and the imaging lens 21 of the video camera 2. Its focal point is positioned at about the entry shutter 21a of the camera lens 21. The camera lens 21 together with the tele-lens 3 forms a tele-centrical imaging optics, which "sees" each point of the measured object M under essentially the same observation angle of essentially 0° and images it onto the light converter element array or the image sensor 22 of the video camera 2. The aperture angle ($\omega$) which is essentially the same for all image points of the measured object M is determined by the dimensions of the entry shutter 21a of the camera lens 21 and is preferably at most about 5°. By way of the tele-lens 3, the camera lens 21 sees a virtual measured object M' and is dimensioned therefor and focussed thereon in a manner generally known.

The size of the scanned image points of the measured object M is determined by the resolution of the image sensor 22 of the video camera 2 as well as by the imaging scale of the tele-centric imaging optics 3–21.

The two flash light sources 4 and 5 are respectively positioned at the focal point of the illumination lenses 42 and 52, so that the measured object M is illuminated with two parallel beam bundles 44 and 54. The positioning is selected such that the angles of incidence $\alpha$ of the two parallel beam bundles are essentially 45°+/−5° to the optical axis of the imaging optics or to normal 31 of the measured object M. The geometric conditions defined in international standards for the color measurement are thereby complied with.

In order to achieve a homogeneous illumination strength over the whole illuminated surface of the object M, the two blend filters 43 and 53 are provided. They have a light transparency which decreases from the outside in, which compensates in a generally known manner, the unavoidable drop of the light intensity at the margin of the beam bundles. The blend filters can consist of a screened film as is common in the graphics industry, whereby the surface coverage (sizes) of the individual grating points is determined by the required light attenuation. The two blend filters 43 and 53 are positioned preferably directly on the Fresnel lenses 42 and 52, but can of course also be positioned at other locations in the illumination light path.

In the preferred embodiment illustrated in FIG. 1, the video camera 2 is constructed as a black and white camera, which means its image sensor 22 can itself not carry out a color separation. The spectral splitting of the measurement light remitted from the measured object M is here sequentially carried out by the bandpass filters 66 which can be swivelled in front of the camera lens 21 and into the imaging light path 32.

For the measurement of the measured object, the individual bandpass filters 66 of the filter wheel 6 as well as possibly the infrared transparent window and the non-transparent region of the filter wheel are sequentially swivelled into the light path and the flash light sources 4 and 5 are respectively activated at the same time. The image sensor 22 respectively receives the measurement light remitted from the measured object and converts the former into corresponding electrical signals. They are input, amplified and digitalized by the signal processing electronics. After a complete measurement cycle, 16 narrow-band color extracts of the measured object are present in the form of digital raw measured data 71 which together represent the (discreet) remission spectra of the individual scanned image points of the measured objects. Additionally, a dark measured value and infrared measured values are possibly available for each image point, which can be used for reference purposes.

When using an image sensor with, for example, (about) 300,000 light converter elements, the raw measured data include 300,000×16 or 300,000×18 individual measured values. The raw measured data 71 are transferred to the data processor 7 and corrected therein according to different criteria. The result of these correction operations are corrected image data 72, which are then available for further use or evaluation.

The spectral characteristic of interference filters is dependent on the angle of incidence of the light beams. This angle is not constant but dependent on the position of the measured image points on the measured object. However, it can be calculated from the position of the respective image point and in turn the actual reflective filter characteristic for the respective image point position can then be determined therefrom. The spectral values can be determined by interpolation for the nominal wavelengths, for example, 400, 420, 440 . . . 680, 700 nm. Therefor, the angle dependency of the filter characteristics can be corrected by recalculation. This is further discussed below.

In the above mentioned embodiment, the measured object M is spectrally measured (in discreet steps). This results in universal measurement data which can be used for any calorimetric evaluation. However, instead of measuring the complete spectrum, for example, only a few color extracts can be measured, for which correspondingly fewer color filters would then be required. For example, the standardized R, G, B-filters or X, Y, Z-filters according to CIE can be used. The result of those measurements would then be R, G, B-values or X, Y, Z-values for each individual image point of the measured object M.

Instead of the sequential arrangement with the filter wheel 6, a simultaneous arrangement can also be provided in an alternative embodiment of the measurement device in accordance with the invention. Such can then be realised, for example, by using a color-enabled video camera or a color-enabled image sensor. Color-enabled image sensors typically have integrated color filters which are positioned directly on each light converter element. However, for an equal number of light converter elements, the achievable resolution and the light sensitivity are thereby decreased by a factor corresponding to the number of the different color filters (normally 3).

In the case of R, G, B-filters, a higher image resolution relative to classical image sensors can be achieved by providing different numbers of light converter elements for the individual colors. For example, twice as many light converter elements can be provided with a green filter than light converter elements equipped with a red filter or a blue filter. This corresponds to the higher resolution capabilities of the human eye for green compared to red and blue. However, the conversion of the R, G, B-measured values measured with such an arrangement into color measurement numbers according to CIE is possible only approximately.

An analogous arrangement is possible if instead of the R, G, B-filters those with the CIE standardized X, Y, Z-spectral characteristics are used. However, it is difficult to manufacture all these filter characteristics sufficiently exactly on a single chip. Furthermore, the color measurement numbers determined through the use of such filters are only valid for the physical light type actually used during the measurement. The calculation of the color measurement numbers of any light type, as is possible with a spectral measurement, is not possible. Furthermore, a color recipe, for example, based only on X, Y, Z-measured values according to CIE is not possible. An improved resolution analog to the above described R, G, B-arrangement can be achieved in that twice as many light converter elements are provided with a Y filter than with an X or Z filter.

It would theoretically be possible to integrate 16 different narrow band color filters into the image sensor so that a spectral measurement therewith would be possible. However, the practical manufacture of sufficiently narrow band filters and of so many different (interference-) color filters directly onto the light converter elements of a single chip is technologically very difficult. Furthermore, image resolution and light sensitivity would sink to 1/16 of a conventional (color neutral) image sensor.

Another possibility for the simultaneous measurement of the whole spectrum consists, according to a further aspect of the invention, in the use of several video cameras, each of which measures a small spectral region of about 20 nm bandwidth and which are grouped, for example, in a 4×4 matrix about the optical axis of the tele-lens. Such an arrangement enables the complete resolution of the image sensors used and also has the full light sensitivity. However, it is disadvantageous that no exact parallel tele-centrical projection is possible for all cameras. Furthermore, the cameras due to their eccentrical positioning have different geometrical registrations. However, they can be corrected by calculating a corresponding transformation of the image co-ordinates.

Figure 2:
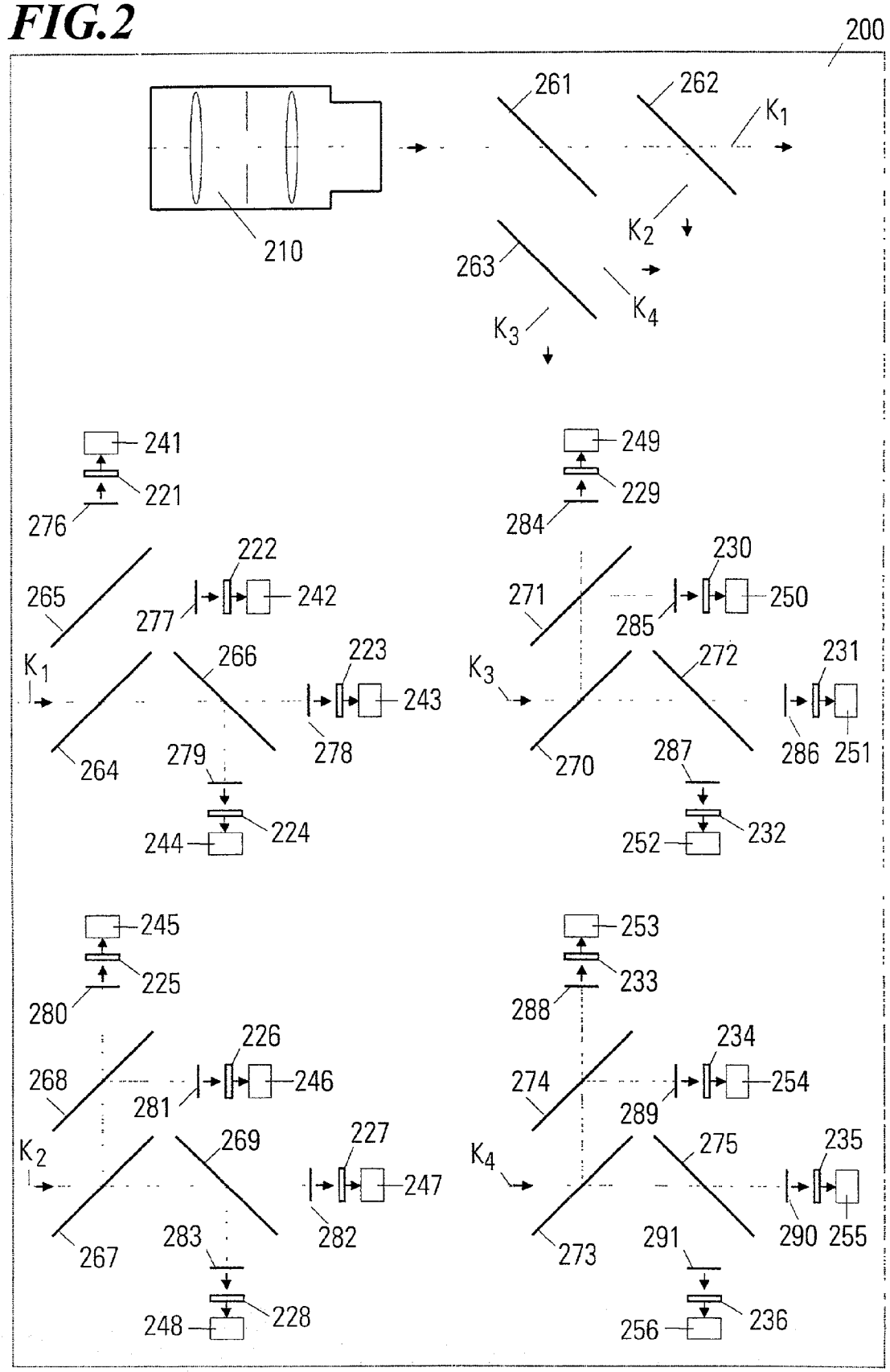
FIG. 2 is a schematic sketch of a spectral video camera of a second embodiment of the measurement device in accordance with the invention.

According to a further preferred embodiment of the measurement device in accordance with the invention, a simultaneous spectral measurement can be realized by use of a specially constructed spectral-video-camera. A principal schematic of such a spectral video camera is shown in FIG. 2.

The essential feature of the camera referred to as a whole by 200 consists in that it does include not only a single but 16 similar image sensors 221–236 and corresponding associated signal processing electronics 241–256 as well as a color-selective beam splitter arrangement 261–291 essentially realised by interference mirrors, which splits the measuring light coming from the imaging lens 210 of the camera 200 into 16 narrow-band spectral regions and directs each spectral region onto respectively one of the image sensors 221–236. The signal processing electronics 241–256 can of course also be combined into a single unit.

Since it is difficult in practice to make the wavelength region transitions of interference mirrors sufficiently narrow band, according to a further aspect of the invention, the measuring light is first split by way of three semi-transparent mirrors 261–263 in a manner generally known and color neutral into 4 channels $K_1$ to $K_4$ of 25% intensity each. Three color-selective beam splitter mirrors 264–266, 266–269, 270–271 and 273–275 are positioned in each of these four channels $K_1$ to $K_4$, which divide each channel into 4 spectral ranges. For a clean band width delimitation and exact adaptation of the spectral characteristics, two bandpass filters 276–291 with a bandwidth of about 20 nm are respectively located after 8 of these color selective beam splitting mirrors. Overall, the spectral regions or bandpass filters cover the wavelength range of 400–700 nm. Image sensors 221–236 are positioned immediately after the bandpass filters.

FIG. 1 shows the transition wavelengths of the exemplary color selective beam splitting mirrors 264–266, 266–269, 270–272 and 273–275 and the mean wavelength of the respectively following bandpass filters 276–291.

TABLE 1

| Beam Splitting Mirror | Transition Wavelength | Bandpass Filter | Mean Wavelength |
|---|---|---|---|
| 264 | 520 | | |
| 265 | 440 | 276 | 400 |
| | | 277 | 480 |
| 266 | 600 | 278 | 640 |
| | | 279 | 560 |
| 267 | 540 | | |
| 268 | 460 | 280 | 420 |
| | | 281 | 500 |
| 269 | 620 | 282 | 620 |
| | | 283 | 580 |
| 270 | 560 | | |
| 271 | 480 | 284 | 440 |
| | | 285 | 520 |
| 272 | 640 | 286 | 680 |
| | | 287 | 600 |
| 273 | 580 | | |
| 274 | 500 | 288 | 460 |
| | | 289 | 540 |
| 275 | 660 | 290 | 700 |
| | | 291 | 620 |

The color neutral semi-transparent mirrors are preferably realized in a generally known manner by the interfaces of essentially about semi-cube-shaped glass prisms. Analogously, the color selective beam splitting mirrors which are realized by interference filters are applied onto interfaces of glass prisms. The bandpass filters are also applied directly onto the glass prisms and the image sensors are mounted directly onto the glass prisms. The individual glass prisms are connected with optical contact so that the losses caused by medium transitions are prevented. The glass prisms are mutually three-dimensionally positioned and oriented such that a compact configuration is created with space for all image sensors.

The beam splitter can also be positioned directly following the tele-lens. Although one then needs a lens for each channel, the smaller aperture angles of such an arrangement are advantageous.

With ideal beam-splitter mirrors in a 1–2–4–8-arrangement, it is principally possible to split the spectrum into 16 spectral regions of 20 nm bandwidth without losses so that each inner sensor receives 100% of the light (of its wavelength region). The band characteristics are thereby determined only by the mirror interference layers so that no additional bandpass filters are required.

Table 2 shows the transition wavelengths of such a 1–2–4–8-arrangement of (ideal) beam splitter mirrors as well as the mean wavelengths of the resulting spectral regions.

TABLE 2

| Transition Wavelengths [nm] Interference Beam Splitter | Mean Wavelengths [nm] Spectral Regions |
|---|---|
|  | 400 |
|  | 410 |
| 430 |  |
| 470 |  |
| 550 |  |
|  | 420 |
|  | 440 |
|  | 450 |
|  | 460 |
|  | 480 |
|  | 490 |
| 510 |  |
|  | 500 |
|  | 520 |
|  | 530 |
|  | 540 |
|  | 560 |
|  | 570 |
| 590 |  |
| 630 |  |
|  | 580 |
|  | 600 |
|  | 610 |
|  | 620 |
|  | 640 |
|  | 650 |
| 670 |  |
|  | 660 |
|  | 680 |
|  | 590 |
|  | 700 |

A simultaneous video camera with 16 spectral regions is very expensive to manufacture. A compromise between such a spectral camera and an X, Y, Z-three region camera is a camera with, for example, seven spectral regions which can be built with corresponding filters. Five filters thereby have a bandwidth of 30 nm each and mean wavelengths of 470, 500, 530, 560, and 590 nm. A filter covers the wavelength region of 400–470 nm and images the Z-characteristic according to CIE in the region of 400–450 nm. A seventh filter covers the wavelength region of 590–700 nm and images in the region of 620–720 nm the X-characteristics according to CIE. With the mentioned filters, the X, Y, Z-characteristics according to CIE can be well reproduced by calculation, which is important for an absolutely exact color measurement. A further filter can be provided which lies in the infrared region and therefore cannot be used for the determination of color measurement numbers. However, this infrared filter allows in a manner known in the art further information on the measured object, for example, whether an image point appears black because of overprinting of the three colors cyan, magenta and yellow or because it is printed with black ink.

The raw measured data 71 (which include, for example, about 300,000×16 or 300,000×18 individual data) are, as already mentioned, transmitted to the data processor 7 and corrected therein according to different aspects. The results of those diverse correction operations are corrected image data 72, which are then available for further use.

Before the actual correction operations in the data processor 7 as described below, the raw measured data 71 are of course first corrected with respect to the image sensor 22, in that the dark measured values are subtracted and the individual CCD-elements of the image sensor 22 are linearized. This pre-correction is generally known and practiced for measurements with image sensors, especially CCD image sensors, and is therefore not described in further detail.

Geometry Correction

Figure 3:
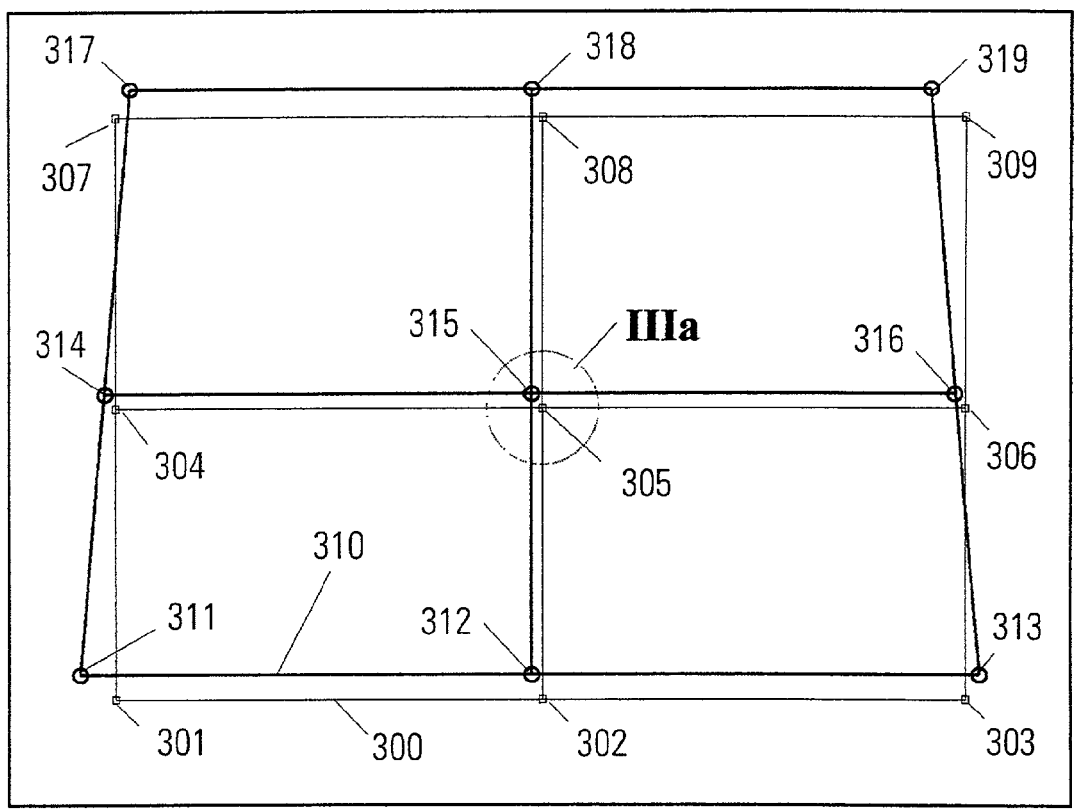
FIG. 3 is a sketch illustrating the geometric rectification of the data of the measured object.

The optical imaging system of the measurement device is generally not absolutely perfect, but causes a (ideally as small as possible) geometric distortion which must be corrected before all further operations. FIG. 3 illustrates the procedure in this respect.

A test image is measured with the measuring device, which includes a test pattern in the form of a rectangular frame and a cross centered in the frame. The corners of the frame and the intersections of the frame with the cross define 9 reference points, which are used for the determination of the geometric distortions. The theoretical position and shape of the test pattern is referred to in FIG. 3 by reference numeral 300, the corresponding reference points are labeled 301–309. The actually measured test pattern (and distorted by the imaging system) is labeled with reference number 310, the corresponding reference points are labeled 311–319. As is apparent from (the highly exaggerated illustration of) FIG. 3, the imaging system in this example, caused a position shift in 2 dimensions as well as a trapezoid distortion.

Figure 3A:
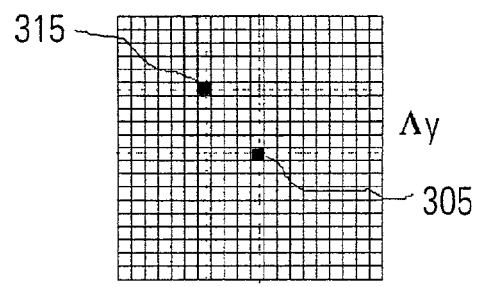
FIG. 3A is an enlarged portion of FIG. 3.

The position deviations $\Delta X$ and $\Delta Y$ relative to the nominal positions (points 301–309) are determined for each of the nine reference points 311–319 as is apparent from FIG. 3a. In the next step, the position deviations for each individual image point of the whole test image are calculated by interpolation from the position deviations of the nine reference points. According to experience, the position deviations of closely adjacent image points are not very different. Thus, according to one aspect of the invention, several, for example 8×8 adjacent image points, are respectively combined into a geometry correction region and the position deviations are calculated only for those geometry correction regions. If one assumes a total of 480×640 image points, this results in about 60×80=4,800 regions. The (calculated) position deviations $\Delta x$ and $\Delta y$ of those 4,800 geometry correction regions are then saved in a geometry correction table. A portion of an exemplary geometry correction table is illustrated in Table 3 $\Delta x$ and $\Delta y$ values are arbitrary).

Of course, other test patters can also be used for the determination of the geometric distortion of the imaging system.

For the geometric correction of the measured object, the geometry correction region to which an image point belongs is determined for each image point (by way of its image point coordinates) and the position deviation Δx and Δy for the respective geometry correction region obtained from the geometry correction table. The actual correction is then carried out in the manner already known in that the measured value of the respective image point is replaced by the measured value of the image point displaced by the position deviation (or by a value interpolated from the surrounding points for non-integer pixel spacings).

TABLE 3

| Region Number | Image Points | Δx (in pixel) | Δy (in pixel) |
|---|---|---|---|
| 1 | x1 ... x8, y1 ... y8 | 3.25 | −5.75 |
| 2 | x9 ... x16, y1 ... y8 | 3.2 | −5.7 |
| And so on | and so on | and so on | and so on |

The further correction measures described below are carried out after the geometric rectification of the measured object, for each individual spectral channel and separately in each respective spectral channel.

A first important correction measure is a contrast correction. Because of the properties of real (which means non-ideal) lenses, filters, closure windows of the image sensor, etc. each image point of the measured object provides a non-negligible contribution to the brightness of all other image points. These contributions are distance dependent on the one hand and location dependent on the other and overall are so large that the demanded measurement accuracy (less than 1 dL*) cannot be achieved. (dL* is the unit of the brightness error in the CIE-L*a*b* system). This is where the contrast correction applies.

The contrast correction includes at least a so-called scattered light correction wherein for each image point the (distance dependent) scattered light influence of the other image points on the respective image point is subtracted. The processing requirements, for this (according to conventional methods) would be enormous and impractical (for an assumed 300,000 image points, 90 billion multiplications and as many additions as well as the one time determination of the 90 billion multiplication factors). Consequently, according to an essential aspect of the invention, only a relatively small region (for example 16×16 pixel) surrounding the respective image point can be used for the scattered light correction, and the correction carried out at full resolution only in an inner core region (for example 8×8 pixel) within this surrounding region. Outside this region, the correction is carried out with binary decreasing resolution. Further details are provided below.

Preferably, the contrast correction also includes a (preceeding) so-called reflex correction. In this correction measure—which represents a special form of a scattered light correction—especially the point-symmetrical reflection images (ghost images) produced by the camera lens are subtracted from the measured data of the measured object. The (mainly location dependent) reflex correction is carried out by way of reflex correction coefficients determined from test images and is also further described further below. The reflex correction is carried out before the scattered light correction.

White Normalization

A further important correction measure is the white normalization. Even when the image illumination of the measured object is as constant and homogeneous as possible, a generally known white normalization with the help of a white reference image is required for an exact remission measurement. A white reference image is understood to be a recording (measured remission values) of a homogeneously white (physical) image with known reference remission values in each spectral channel (determined for example by way of a separate spectrophotometer)' which recording is made with the image sensor 22, is scattered light corrected as described above, and is stored. The homogeneously white physical image can be constructed as a component of the measurement device which is to be brought into the measurement light path in the plane of the measured object, or is to be again removed therefrom.

The quotient of the remission value of the measured object to the corresponding (stored) remission value of the white reference image is calculated for each pixel (in each spectral channel) for the white normalization. The result are normalized remission values for each image element in each pixel. Absolute remission values are obtained by multiplication of the so normalized remission values with the corresponding (known) reference remission values (absolute white calibration values) of the homogeneously white (physical) image. The white normalization is a correction measure generally known and therefore does not need any further explanation.

Border White Normalization

A further important correction step after the contrast correction or after the white normalization, consists in a so called white border normalization. It is a goal thereof to compensate the integral illumination variations from measured object illumination to measured object illumination, which are always present in practice. A defined border region of the homogeneously white (physical) image already mentioned in connection with the white normalization is used herefor, or a correspondingly, homogeneously white object mask with preferably equal white shade is used as the image. Alternatively, a white border region of the measured object and delimiting the same can be used. If the border region of the homogeneously white physical image is used, it can serve as an object mask at the same time.

The actual mean brightness (mean of the remission values) of the border region is determined from the actually measured remission values of the pixels belonging to the border region used. Furthermore, the corresponding mean brightness for a corresponding border region of the white reference image is determined (from the stored data). The quotient of the mean brightnesses of the border region of the white reference image to that of the actually measured border region is used as correction factor, with which the data measured or the measured object are multiplied for the white border normalization, so that the new white border brightness of the actual measurement corresponds with that of the white reference image after the white border normalization. By way of the white border normalization, the mean brightness of the white border regions is raised or lowered to the white calibration value and integral illumination variations between the individual measured object illuminations are compensated in this manner.

The image data corrected in this way can then be analyzed in any way or further processed. Especially, the color measurement numbers of the individual image points of the measured object can be calculated therefrom in a generally known manner and used, for example, for the control of a printing machine.

Reflex Correction

Figure 4:
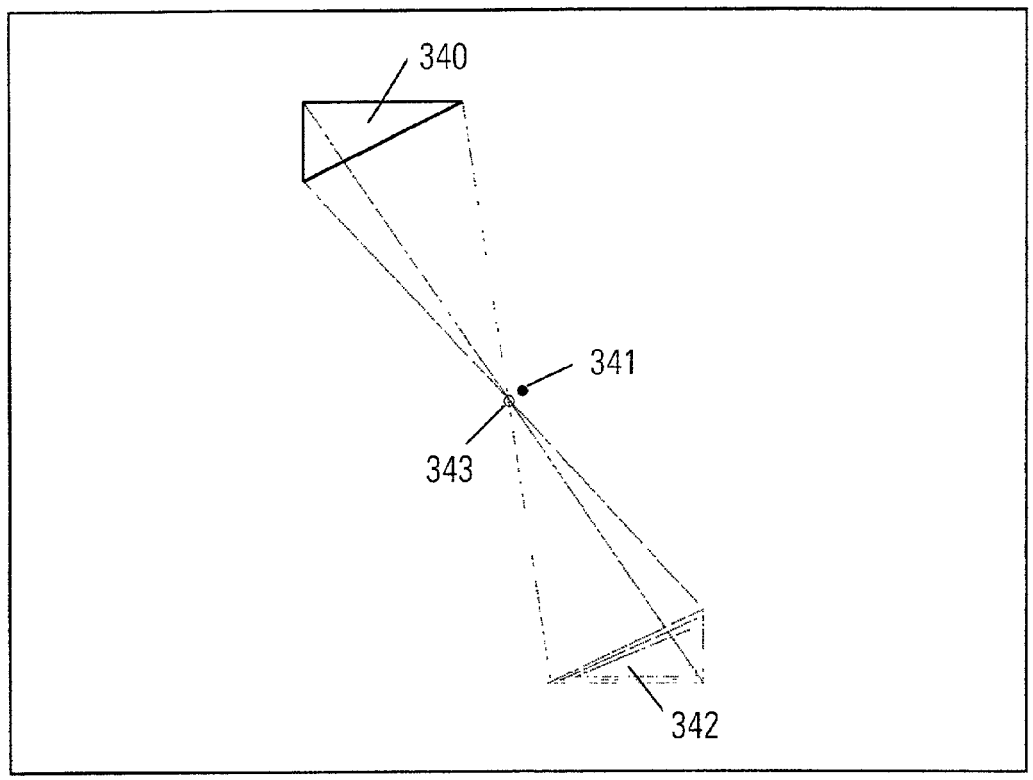
FIGS. 4 and 5 show two sketches for illustration of the reflection correction.

As already mentioned, the imaging optic, especially the lens of the CCD camera, produces a reflection image, which generally, relative to the optical axis or relative to the image center, is point symmetrical to the actual image content. Although the reflection image is of relatively low intensity (in the order of 0.2% of the brightness of the original image) it is clearly detectable. Furthermore, the reflection image is out of focus. Depending on the centering of the lenses or optics of the imaging system, the center of symmetry can also be located slightly outside the image center and furthermore, the reflection image can be somewhat smaller or larger than the original image. FIG. 4 illustrates a recording of a measured object produced with the measuring device, which includes a single bright triangle 340, that is black for the remainder. The image center is labeled 341. As is apparent, the recording includes a reflection image 342, which relative to a center of symmetry 343 located here somewhat beside the image center 341, is point-symmetrical to the triangle 340. In the example chosen, the reflection image 342 is of about the same size as the triangle 340 so that the enlargement is about 1.0. The reflection image 342 is relatively out of focus, which is indicated in FIG. 4 by the triple broken illustration. The brightness of the reflection image 342 is about 0.2% of the brightness of the triangle 340.

Measurements of different test images of the types shown in FIG. 4 have shown that (for a given measurement device) the brightness of the reflection image is only marginally dependent on the distance and that the distance dependency can be linearly approximated with sufficient precision for practical purposes. For example, the brightness of the reflection image in the image points spaced furthest from the centre of symmetry is about 0.25% and in the vicinity of the centre of symmetry about 0.2% of the brighmess of the corresponding image points of the original image. The out of focus condition of the reflection image corresponds to a low pass filtering with about +/−56 to 64 pixel width.

In preparation for the reflection correction, the location of the centre of symmetry 343 of the reflection image as well as the relative brightness of the reflection image in the central and peripheral image region and a possible enlargement or reduction factor are determined as correction parameters by empirical measurement of several test images.

Figure 5:
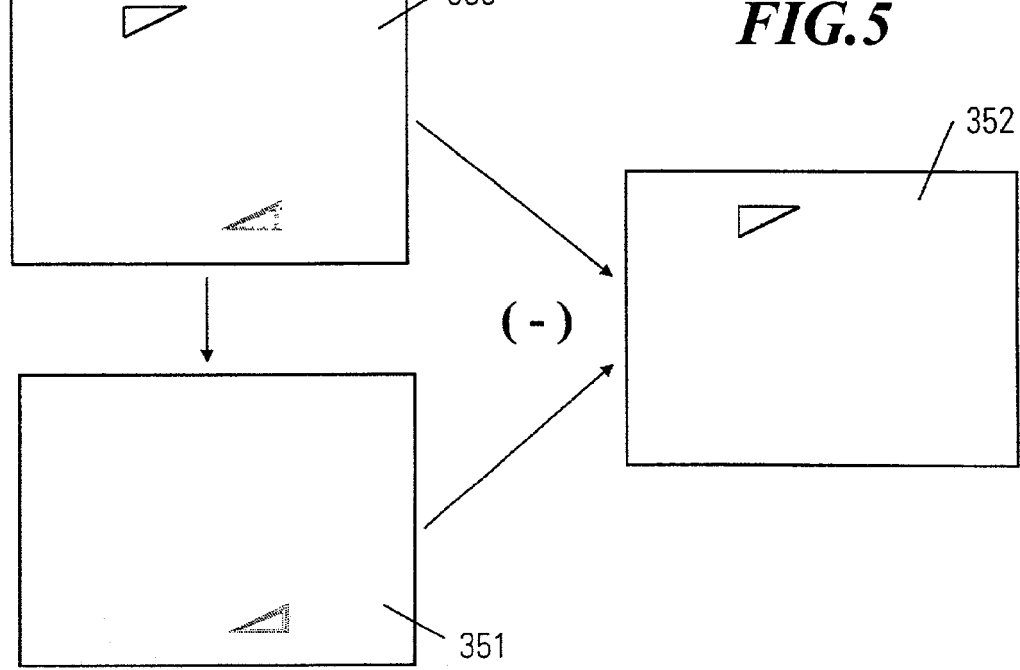

The reflection correction is then carried out by way of the empirical correction parameters in that an artificial reflection image is reduced from the measured image by mirror copying about the centre of symmetry and low pass filtering (bringing out of focus or smudging), possibly enlargement or reduction (interpolated linearly between the extreme values), as well as distance dependent reduction of the brightness, which artificial reflection image is then subtracted from the original image. This is illustrated in FIG. 5. The image produced from the uncorrected measured data is labeled 350, the calculated "artificial" reflection image with 351 and the reflection corrected image with 352. The low pass filtering is carried out in a known manner by a continuous formation of a mean over the respectively about +/−(64/2) adjacent image points (in both dimensions). The mirror imaging and enlargement/reduction is carried out by coordinate transformation according to principally known image processing methods. The correction parameters determined according to the above are first approximations and generally still do not provide an optimal correction. In practice, the correction parameters must be iteratively adapted one or several times until the reflection correction provides satisfying results (testing by display of leftover brightness and errors). However, once the optimal correction parameters are found, they can be maintained without further changes (for the given measurement device).

The above described reflection correction is relatively calculation intensive. According to an important aspect of the invention, the calculation effort can be reduced in that the calculation of the artificial reflection image is carried out at a lower resolution. Which resolution results in the ideal compromise between calculation effort and correction precision must be determined through experimentation. In a practical realization of the measurement device, a resolution of ⅛ of the full resolution (of the uncorrected image) has proven suitable, whereby the calculation effort was reduced by a factor of 64. The calculation of auxiliary images with a more coarse resolution is carried out in the same manner as described further below in connection with the scattered light correction.

Scattered Light Correction

The scattered light correction for each image point subtracts from the brightness value (remission value) of the respective image point the distance dependent brightness contribution of all image points surrounding the image point. The brightness contribution $\Delta R_i$, J received by an image point j from an image point j is calculated as $\Delta R_{i,j} = k_{i,j} * R_j$. $R_j$ is thereby the remission value of the image point j, and $k_{i,j}$ is a coefficient depending on the distance between the image points i and j, which of course must be determined beforehand. For an arrangement of N*M image points, which are numbered from 1–N*M, the contribution of the surrounding points is calculated as follows for each individual image point i:

$$\Delta R_i = \sum_{j=1}^{N \cdot M} k_{1,j} * R_j \qquad \text{Formula 1}$$

The scattered light corrected remission value $R'_i$ is $R_i - \Delta R_i$. As is easily apparent, $(M*M)^2$ coefficients and a corresponding number of multiplications and additions are required for the calculation of the corrections. For 300,000 image points, the required calculation effort would be gigantic and completely impractical as already mentioned.

In accordance with the invention, one now proceeds in the manner that a correction at full resolution is carried out only for a relatively small image region (typically 16×16 pixel) and within the same for an even smaller core region (typically 8×8 pixel). Outside the mentioned image region, the correction is carried out preferably with binary graduation and at decreasing resolution with increasing distance. A graduation of the resolution other than binary is of course also possible.

For this purpose, for example, five auxiliary images with binary graduated resolution and with fixed relation to the image border are calculated from the image with full resolution (raw measured data or already reflex corrected data). The image with full resolution defined by the raw data or the reflex corrected measured data is in the following referred to as the original image. The auxiliary images have ½, ¼, ⅛, 1/16 and 1/32 of the resolution of the original image. The corrections are determined from the original image and the auxiliary images. For the calculation of an auxiliary image with the next lower (half) resolution, four adjacent image points are combined in a generally known manner, whereby the mean remission of these four image points represents the remission value of the corresponding image points of the coarser auxiliary image.

For the following and purely for exemplary illustration purposes, a maximum resolution (set by the image sensor) of 480×640 is assumed for the original image, which corresponds to 307,200 image points. Accordingly, the five auxiliary images then have resolutions of 240×320 (76,800 image points), 120×160 (19,200 image points), 60×80 (4800) image points, 30×40 image points), and 15×20 (300 image points).

Core regions respectively including 8×8 pixels are now selected so that they on the one hand cover the whole image (of highest resolution) without overlap and without gaps and on the other hand fit into the grid of the auxiliary images with binary graduated resolution. The positions or coordinates (for example of a corner point) of the core regions relative to the grid of the image with full resolution and of each auxiliary image are stored. The core regions overlap with the image points of the auxiliary image with ⅛ resolution.

According to the invention, the scattered light correction is calculated separately for each resolution. For each original image with full resolution and for the auxiliary images with the binary graduated resolutions, 6 scattered light contributions from defined analysis regions are calculated (for each image point of the original image). The 6 scattered light contributions are added up to a total scattered light contribution and the latter is finally subtracted from the raw data of individual image points.

The following operations are with respect to an 8*8 core region and are carried out (sequentially) for all core regions.

Figure 6:
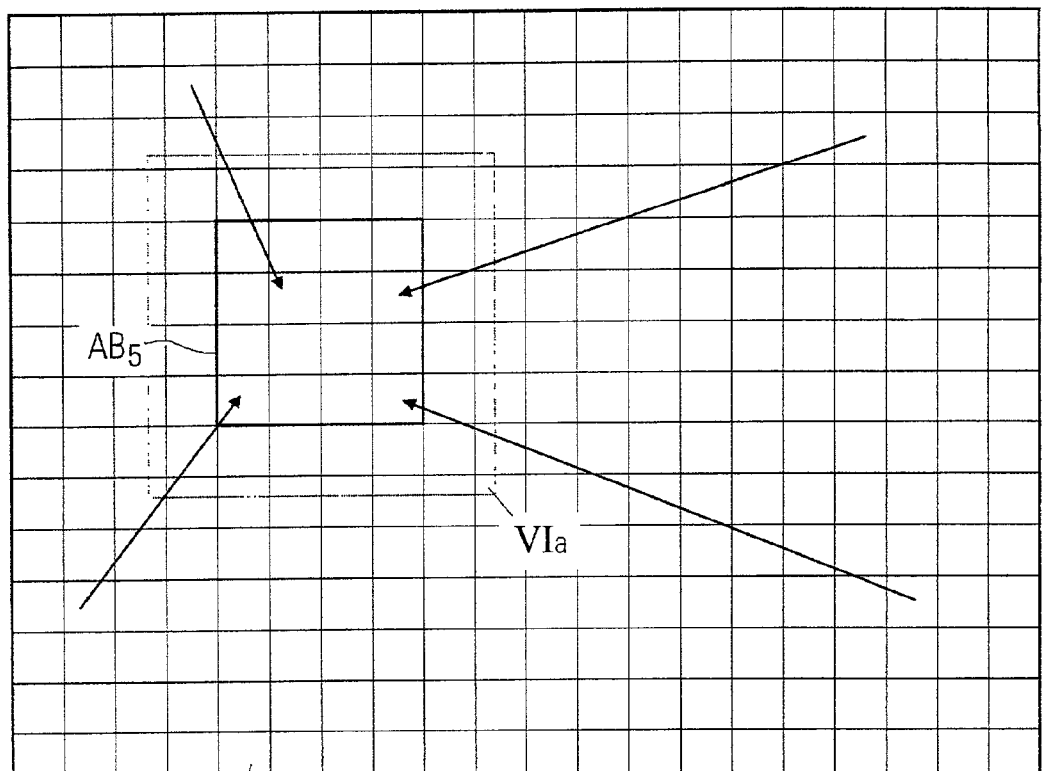
FIG. 6 is a sketch for illustration of the scattered light correction.
Figure 6:
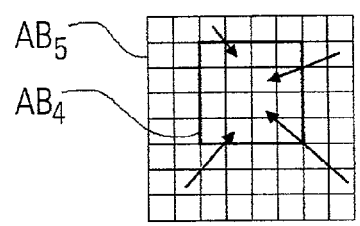
Figure 6:
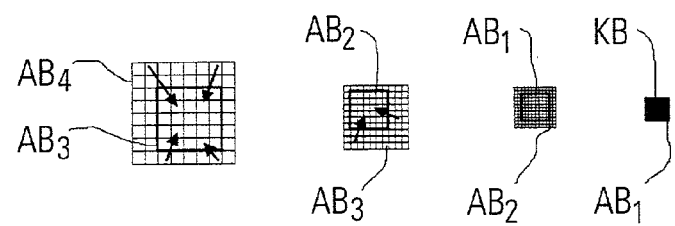
Figure 6A:
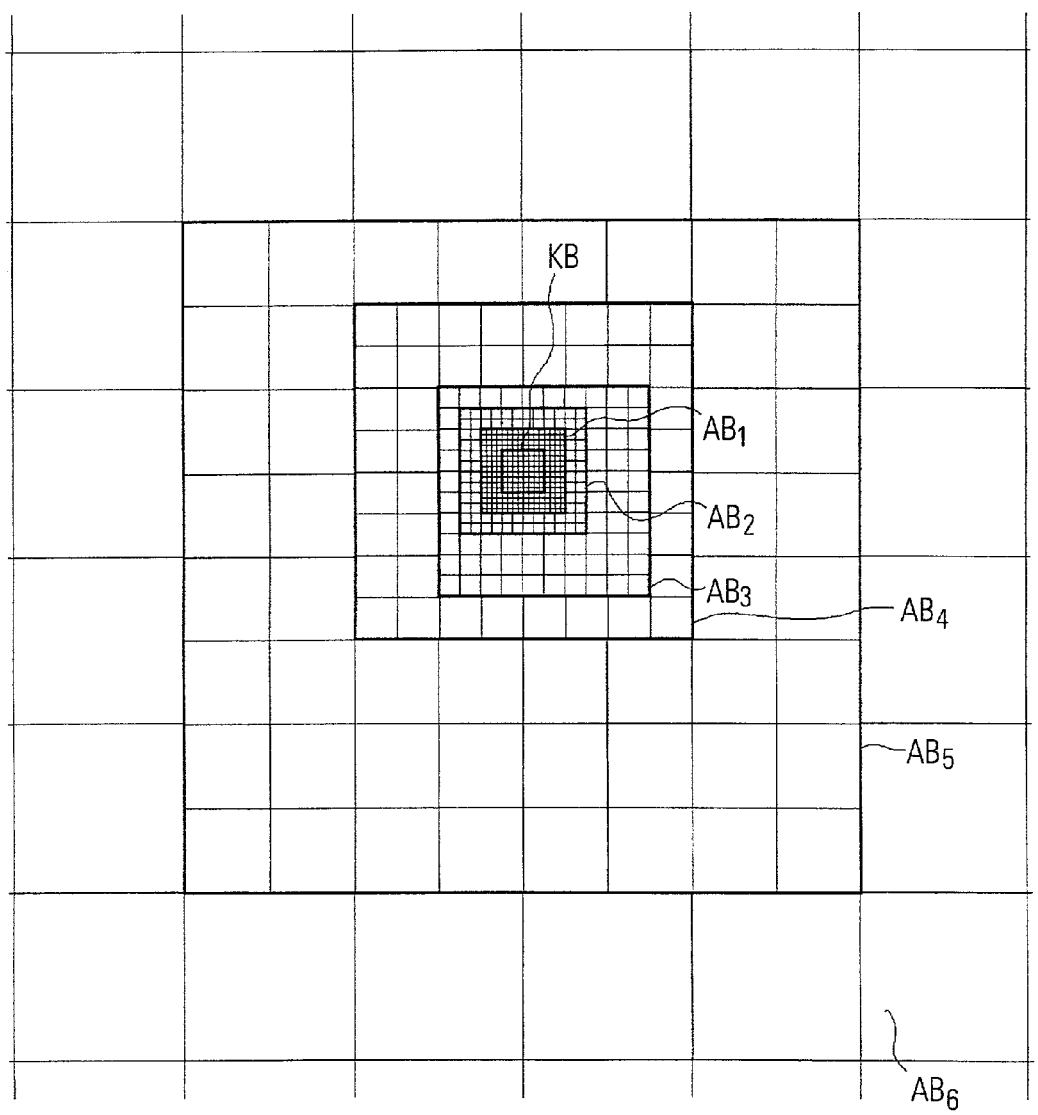
FIG. 6A shows an enlarged portion of FIG. 6.

For the calculation of the scattered light correction of any image point of the original image with the full resolution, that 8*8 core region KB (out of the previously defined core regions) is determined in which the image point to be corrected is located. Subsequently, one analysis region $AB_1$–$AB_6$ is respectively set for each of the original image and the five auxiliary images with binary graduated resolution, which on the one hand covers the core region KB and on the other hand corresponds with the grid of the respectively coarser auxiliary image, whereby the region limits must coincide with the image element limits of the same resolution. The same auxiliary images of graduated resolution can thereby be used for all image points of the image. A possible exemplary determination of the six analysis regions is illustrated in the FIGS. 6 and 6a. The outermost analysis region $AB_6$ covers the whole auxiliary image with 1/32 resolution (FIG. 6). The innermost five analysis regions $AB_1$–$AB_5$ are significantly smaller (FIG. 6a). The following Table 4 summarizes the characteristic data of the individual (exemplary) regions:

TABLE 4

| Region | Resolution | Dimension | Number of Elements |
|---|---|---|---|
| Core Region KB | 1/1 | 8*8 | 64 |
| Analysis Region 1 | 1/1 | 16*16 | 256 |
| Analysis Region 2 | 1/2 | 12*12 | 144 |
| Analysis Region 3 | 1/4 | 10*10 | 100 |
| Analysis Region 4 | 1/8 | 8*8 | 64 |
| Analysis Region 5 | 1/16 | 8*8 | 64 |
| Analysis Region 6 | 1/32 | 15*20 | 300 |

The determination of the dimensions of the analysis regions is carried out empirically, so that a sufficient scattered light correction results. The larger the analysis regions with higher resolution, the better the correction, whereby however the calculation effort increases at the same time. The exemplary dimensioning according to Table 4 delivers the required correction accuracy with a justifiable calculation effort.

The relative location of the core region and the analysis regions within the respectively larger analysis regions of course change depending on where the core region is located in the image or the outermost analysis region. It is an essential condition that the region limits correspond with the grid of the respectively coarser auxiliary image and that the region limits coincide with the pixel limits of the same resolution. With this condition (and the once fixed dimensions), the resolution regions—apart from equivalent symmetrical solutions—can be clearly determined (calculated) and stored.

Scattered Light Correction of a Core Region of 8*8 Pixels:

Starting with the largest image resolution (15*20) the scattered light contributions of the image points of the coarsest analysis regions $AB_6$ are calculated onto the image points of the inwardly next inner analysis region $AB_5$ (compare also FIG. 6). Since overall 16 image points of the analysis region $AB_6$ are located within the analysis region $AB_5$, 16*(300−16)=4544 correction coefficients are required for the calculation of the scattered light portions for the actual analysis region $AB_5$, and 300*300=90,000 for the whole auxiliary image at a resolution of 1/32. The scattered light contributions of the analysis region $AB_6$ are stored temporarily.

Furthermore, the auxiliary image data of the analysis region $AB_5$ are copied into a data buffer and the scattered light contributions of the annular analysis region $AB_6$ subtracted therefrom. This is carried out in preparation of the scattered light calculation for the inwardly next analysis region, so that the values relieved of the scattered light of the annular analysis region $AB_6$ are available, since only those values produce a further scattered light portion for the subsequent analysis regions.

The scattered light contributions of the image points of the analysis region $AB_5$ which are already relieved of the scattered light contributions of the analysis region $AB_6$ (data from the data buffer) are now calculated in an analogous manner onto the image points of the inwardly next analysis region $AB_4$. The 16 image points of the analysis region $AB_5$ are located in the analysis region $AB_4$, so that 16*(64−16) =768 correction coefficients are required and 64*64 for the whole analysis region $AB_5$. The scattered light contributions of the analysis region $AB_5$ are temporarily stored and the auxiliary image data of the inwardly next analysis region $AB_4$ are copied into a further data buffer. Furthermore, the scattered light contributions of the annular analysis region $AB_5$ are subtracted in an analogous manner from these auxiliary image data, so that data cleaned of scattered light are again available for the subsequent step.

In an analogous manner, the scattered light contributions of the image points of the (already cleaned of scattered light) analysis regions $AB_4$, $AB_3$, $AB_2$, and $AB_1$, onto the image points of the respectively inwardly next analysis region $AB_3$, $AB_2$, and $AB_1$ and onto each of the 8*8 image points of the core region KB are continuously calculated and temporarily stored. As can be counted by way of FIG. 6a, 975, 2304, 5120 and 16384 or 4096, 10000, 20736 and 65536 correction coefficients are necessary therefor. (With the exception of the core region, only the influence of the surrounding annular region on the inner central region is calculated for each analysis region—compare also FIG. 6).

After completion of the calculations, the six scattered light contributions of the analysis regions $AB_1$–$AB_6$ are respectively present for each of the 8*8 image points of the core region. These six scattered light contributions are added to a total scattered light contribution for each image point of the core region KB, whereby the scattered light contribution of each image point is respectively transferred to four image points of the auxiliary image of the next higher resolution. The total scattered light contribution (or portion) is then subtracted from the (possibly previously reflex corrected) remission value of the respective image point of the core region.

Scattered Light Correction of the Whole Image:

For the scattered light correction of the remaining image points of the original image, the same calculations are carried out for all remaining core regions. According to a further aspect of the invention, always the same correction coefficients (in the here-described exemplary embodiment overall 194464) are used. Of course, for each core region actually only a partial amount (here for example 30095) of the overall 194464 correction coefficients are required. The correction coefficients effectively used for each core region are fixed by the relative positions of the core region and the analysis regions.

As is apparent from the above number examples, the calculation effort for the scattered light correction in accordance with the invention is several orders of magnitude lower than with the classical approach. The scattered light correction is actually only made practical in this manner.

Scattered Light Correction of Individual Image Regions:

In practical applications, often only the spectra and colour measurement numbers of particular image regions are of interest. In those cases, a scattered light correction for only the image points of that image region or those image regions is sufficient. Thus, the scattered light corrections are calculated only for those core regions which include at least one image point of the image regions of interest.

Determination of the Scattered Light Correction Coefficients:

The determination of the correction coefficients required for the scattered light correction is described below.

The $(N*M)^2$ correction coefficients $k_{ij}$ used in the above cited Formula 1 can be organized in a coefficient matrix. When on the other hand $(s_{ij})$ represents a scattered light coefficient matrix, the elements $s_{ij}$ of which describe the scattered light influence $AR_{ij}$ of each image point i on each individual image point j, so that the Formula $AR_{ij}=s_{ij}* R_i$ applies, then the correction coefficient matrix is obviously the inverse matrix of $(s_{ij})$. When the elements of the scattered light coefficient matrix $(s_{ij})$ have been determined, the elements of the correction coefficient matrix can be calculated therefrom by inversion.

The elements of the scattered light coefficient matrix $(s_{ij})$ can be determined by scattered light measurements on test images. For this, one can principally proceed as follows: test images with respectively only one single brightly white image point are used for an image point region of, for example, 16*16 image points, all other image points being black. The remission $R_i$ of the single white point is measured and the remissions $AR_{ij}$ of all remaining image points produced by the scattered light influence of the single white point. The measured values are then inserted into the scattered light matrix formula and the scattered light coefficients $s_{ij}$ calculated therefrom as unknowns.

For a clear determination of the elements of a scattered light coefficient matrix, the same number of independent measurements are required as the number of the independent matrix elements. Correspondingly, at least 194464 measurement procedures would be necessary for the above already mentioned six correction coefficient matrixes of the six resolution steps (which can be calculated as the inverse to the corresponding six scattered light coefficient matrixes) with overall 194464 coefficients. Of course, this is not practical. Furthermore, the extremely low scattered light contributions of individual image points cannot be measured with sufficient precision.

In order to reduce the effort for the determination of the correction coefficients, one makes use of the fact that the scattered light influence within the framework of the precision required here is not location independent but only distance independent. Thus, one proceeds as follows in accordance with the invention.

Eight test images with special scattered light elements are produced and measured (analysed) with the measuring device. Each scattered light element consists (similar to the calibration elements) of a single white annulus. The (mean) radii and annulus widths of the scattered light elements are different for each test image. Overall, eight differently sized scattered light elements are provided, the mean radii of which are, for example, 2, 3, 8, 16, 25, 50, 100 and 200 pixels. The annulus widths vary between about 1 pixel for the smallest and about 40 pixels for the largest annulus. Each test image preferably includes several identical scattered light elements in order to obtain several measurement results and to be able to reduce the measurement error in this manner. Especially the smallest scattered light elements are somewhat critical insofar as the centre of measurement (pixel) is not always exactly at the centre of the annulus. Groups of scattered light elements are therefor preferably provided on these test images, whereby the elements of one group are respectively displaced by ½ or ¼ pixel relative to the pixel raster. In this manner, at least in one scattered light element of the group one pixel is always located sufficiently exactly in the centre of the scattered light element. The measured values from this scattered light element (identifiable by the lowest scattered light) are then used.

Figure 8:
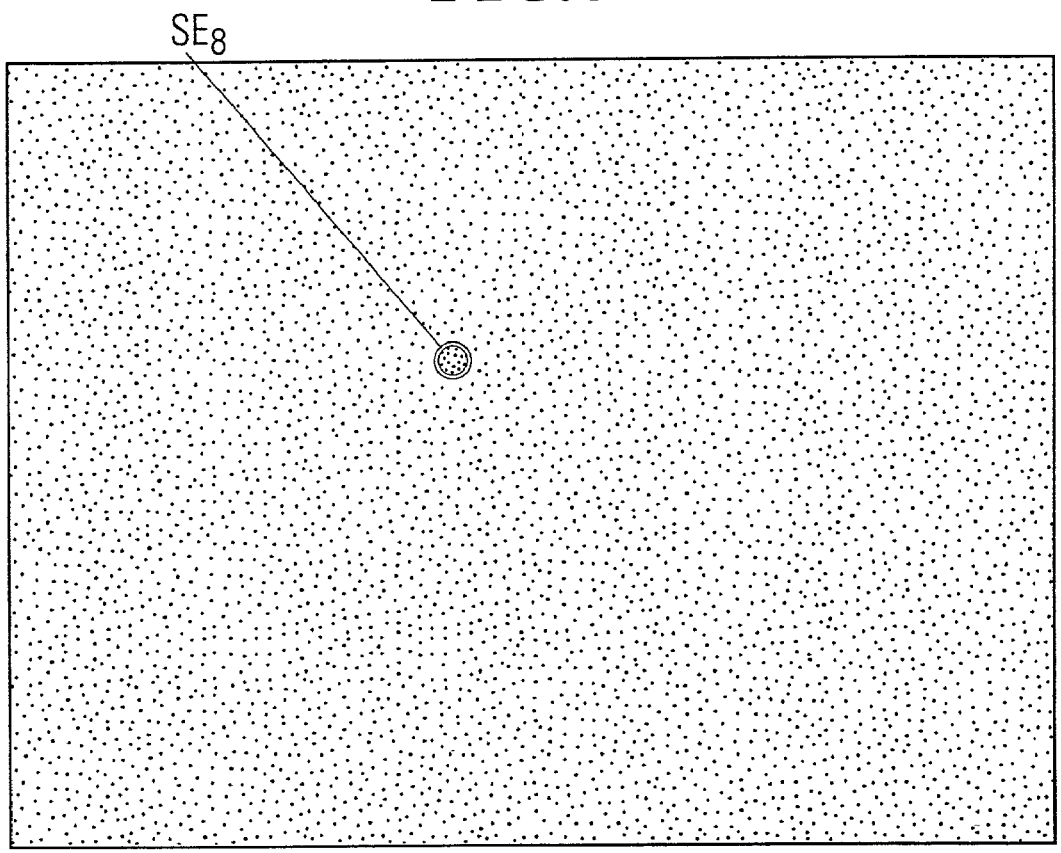
FIG. 8 is a test image with a special scattered light element.
Figure 8A:
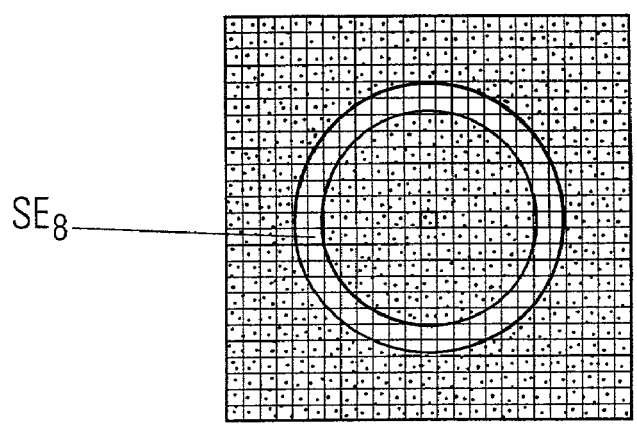
FIG. 8A shows the scattered light element of FIG. 8 in an enlarged illustration.

FIG. 8 illustrates a test image with a single scattered light element $SE_8$; FIG. 8a shows the scattered light element in enlarged illustration.

As already mentioned, the scattered light is measured at the centre of the scattered light elements. The measured scattered light is respectively normalized onto one pixel (measured remission divided by the annular surface in pixel units). The quotient of normalized scattered light to brightness of the white pixels provides the relative scattered light influence and thereby those coefficients of the scattered light matrix which are valid for all those image point pairs which are spaced from one another by the (mean) annular radius of the measured scattered light element.

Figure 9:
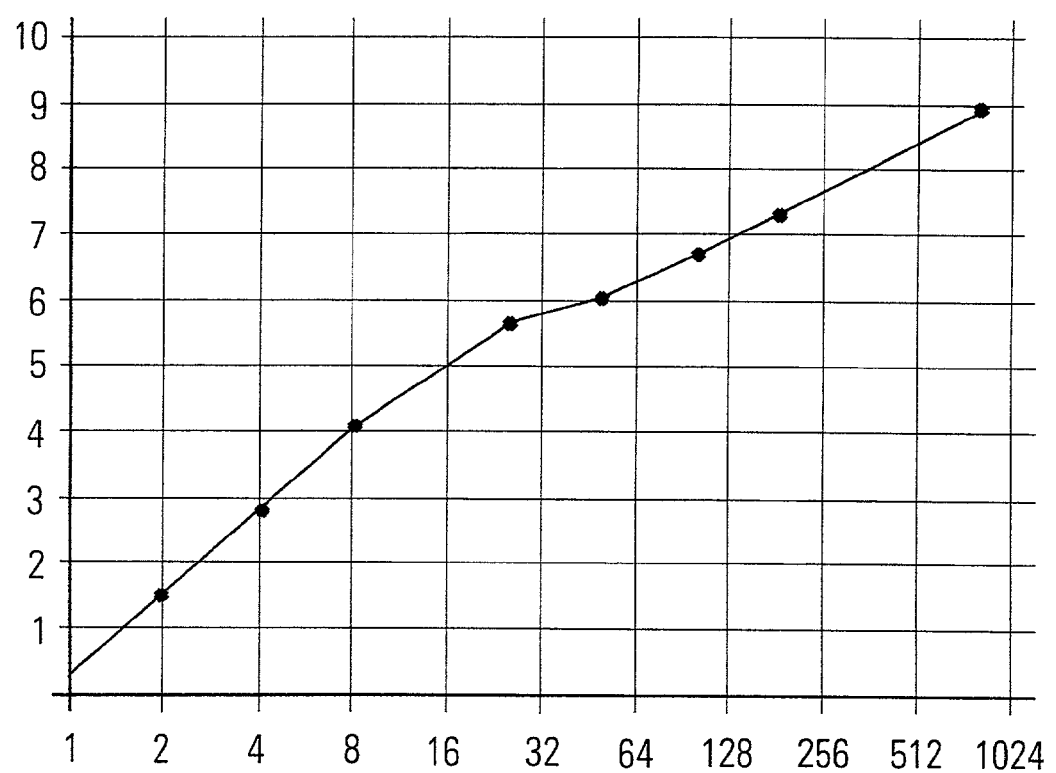
FIG. 9 is a diagram for the illustration of the calculation of scattered light coefficients.

By way of numerous test measurements with scattered light elements of different size, it was found that the scattered light influence decreases at a double logarithmic scale at least in some sections and also overall approximately linear with distance. FIG. 9 graphically illustrates in a double logarithmic scale an exemplary relationship between scattered light and image point distance measured by way of 8 scattered light elements. The abscissa shows the distance in pixel units, the ordinate the negative logarithm of the relative scattered light influence or the scattered light coefficient. For example, the scattered light coefficient at a distance of around 50 pixels is $10^{-5.993}$. At a distance of about 2 pixels, the scattered light coefficient is $10^{-1.564}$, thus already about 4 orders of magnitude larger.

The eight (or more) scattered or adventitious light coefficients for the 8 (or more) pixel spacings defined by the annular radii and measured by way of the 8 (or more) scattered or diffused light elements can now be used as bases for a step by step linear interpolation. The distances of the possible image point pairs are known for each level of resolution (in this example overall 194,464 pairs). By the mentioned interpolation, the associated scattered light coefficients can be calculated with sufficient precision for each occurring pixel distance. Therefore, for each level of resolution results a scattered light coefficient matrix of the dimensions 256*256, 144*144, 100*100, 64*64, and 300*300, overall 194,464 scattered light coefficients, of which of course very many are equal since many image point pairs have the same pixel distance.

The 6 scattered light coefficient matrices so calculated are now inverted and thereby provide the six correction coefficient matrices. They are then multiplied with the respectively associated calibration factor according to the preceding explanations and are then available for the calculation of the scattered light correction. Under the condition that the calculation routines are programmed in a powerful program language, for example, C++, the calculation of the correction coefficient matrices by way of the measured data of the test images can be carried out in a few seconds on an average office computer.

Calibration of the Scattered Light Correction:

The scattered light correction can still be optimized when according to a further important aspect of the invention, a calibration of the scattered light correction is carried out with the goal to minimize the mean square residual error of the correction. Residual error refers to the still present brightness difference (to the theoretically expected value) in an image point after the scattered light correction. For example, the measured brightness (after the scattered light correction) in a black image region should actually be 0. However, upon insufficiently exact correction of the scattered light, a (very small) remaining brightness is still measured, which represents the residual error for the respective image region.

The calibration of the scattered light correction consists essentially in that the scattered light contribution of the six analysis regions is evaluated with (generally different) weights and the weighted sum (in place of the normal unweighted sum) of the individual scattered light contributions is subtracted from the emission value of the image point. This can then be represented by the following Formula 2:

$$\Delta R = G_1 * \Delta R_{AB1} + G_2 * \Delta R_{AB2} + G_3 * \Delta R_{AB3} + G_4 * \Delta R_{AB4} + G_5 * \Delta R_{AB5} + G_6 * \Delta R_{AB6}$$

Whereby $\Delta R$ represents the total scattered light correction of an image point, $\Delta R_{AB1} \ldots \Delta R_{AB6}$ the individual scattered light correction contributions of the individual analysis regions $AB_1 \ldots AB_6$, and $G_1 \ldots G_6$ the previously once determined weighting and calibration factors.

In practice, the scattered light correction contributions are not weighted, but the correction coefficients (of the respective level of resolution) which are used for their calculation are multiplied with the calibration factor associated with the respective level of resolution, for example, the 65,536 correction coefficients of the level of resolution 1/1 with the calibration factor $G_1$, the 20,736 coefficients of the level of resolution ½ with the calibration factor $G_2$, and so on. Due to the linearity of the diverse calculation operations, this provides the same result, but needs to be carried out only once and therefore requires overall less effort.

Figure 7A:
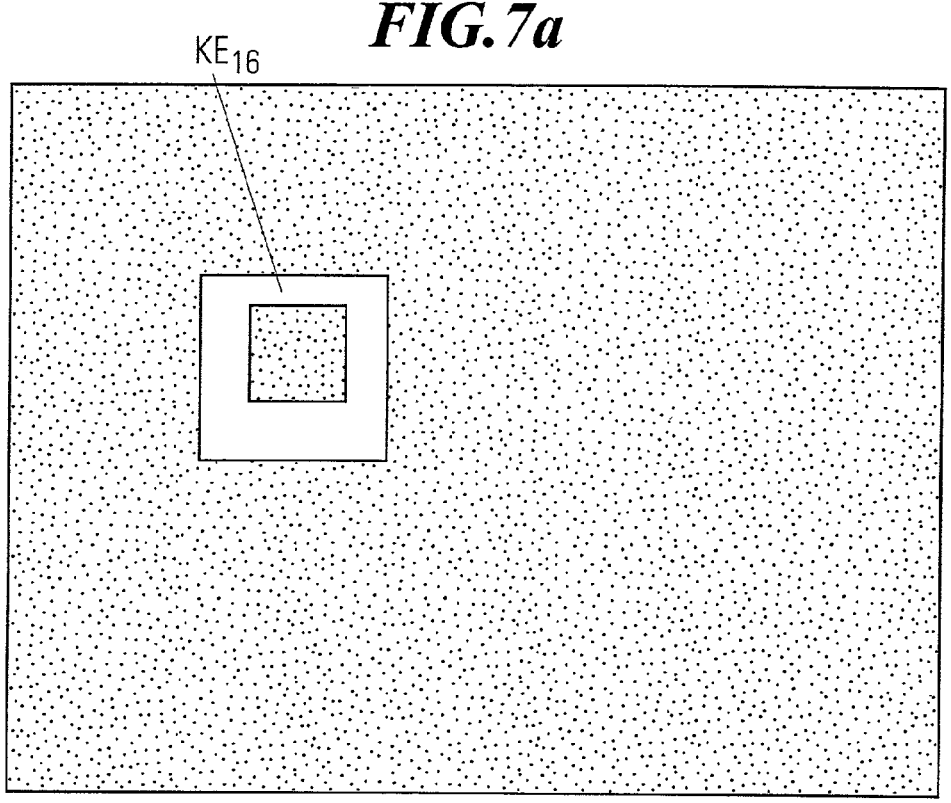
FIGS. 7A and 7B show two test images with respectively one special calibration element.
Figure 7B:
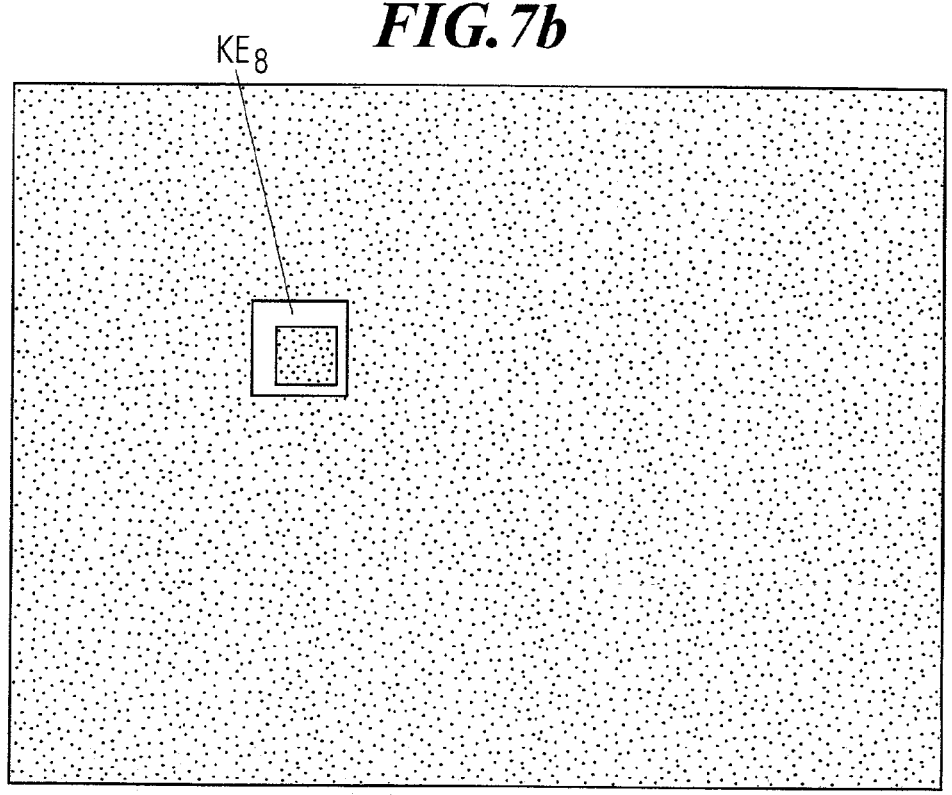

The determination of the calibration factors is carried out by measurement and evaluation of test images with suitable image patterns. The test images are preferably provided with special calibration elements. A separate test image is provided for each resolution with a calibration element adjusted to the resolution. Although the calibration elements principally can be of any construction, it is recommended that the calibration elements are built after the analysis regions in order to guarantee the independence of the measurements. FIGS. 7a and 7b show preferred calibration elements. Two test images are illustrated with a calibration element $KE_{16}$ or $KE_8$ respectively for the levels of resolution 1/16 and ⅛ and the remaining test images or their calibration elements are constructed analogously.

As is apparent, each calibration element consists only of a white (polygonal) annulus. The outer dimensions of the annulus correspond to the analysis region $AB_n$ of the level of resolution n, for which the calibration element is intended (see FIG. 6). The (black) centre of the calibration element corresponds with the inwardly next analysis region or the core region. The calibration element intended for the coarsest level of resolution (1/32) is "degenerate" in so far as no black surface is outwardly adjacent the white ring. The reference point for the measurements or analysis is respectively the core region (8*8 pixel at full resolution) of the (black) centre of the calibration element. (For reasons of graphical representation, the black regions of the test images are presented as a grey pattern). Each test image is now measured and the six scattered light correction conversions of the individual levels of resolution are determined in the core region of the respective calibration element. They are referred to in the following as $S_{n,1}, S_{n,2} \ldots S_{n,6}$, whereby the index n stands for the respective test image or the respective measurement. Overall, at least 6 (in the mathematic sense) independent measurements are required for the determination of the six calibration factors. Furthermore, a dark measurement (white rings covered by black) is carried out for each test image and the corresponding scattered light contributions are determined for the same core regions. They are referred to in the following as $B_{n,1}, B_{n,2} \ldots B_{n,6}$ whereby the index n again stands for the respective test image or the respective measurement. The dark measurement is required, since the black regions of the test images are not ideally black for physical reasons and also create scattered light. Subsequently, two differences $D_{n,1}$, between the contributions $S_{n,1}$ of the illuminated measurement and the contributions $B_{n,1}$ of the dark measurement are formed. Finally, the residual error $F_n$ is then determined (as defined above) for each measurement.

The 6*n differences $D_{n,1}$ and the n residual errors $F_n$ are inserted into the following equation system with the six calibration factors $G_r$ as unknowns:

$$-F_n = G_1 * D_{n,1} + G_2 * D_{n,2} + G_3 * D_{n,3} + G_4 * D_{n,4} + G_5 * D_{n,5} + G_6 * D_{n,6}$$

This equation system which includes at least six equations is solved for the unknowns G1 . . . G6 and the marginal condition that the sum of the squares of the errors becomes minimal (compensation calculation). As is apparent, the equation system can be written as a matrix equation $$(-F) = D(D) * (G) \qquad \text{Formula 2}$$

wherein (−F) represents an error vector with the components −Fn, (G) represents an unknown vector with the components G1 ... G6, and (D) a coefficient matrix with the elements $D_{n,1}$. The matrix equation is solved for the unknowns according to the known rules of the compensation calculation as follows:

$$(G) = [(D)^T * (D)]^{-1} * (D)^T * (-F) \quad \text{Formula 3}$$

wherein $(D)^T$ represents the transposed matrix to (D), and $[(D)^T * (D)]^{-1}$ represents the inverse matrix to the product of the two matrices $(D)^T$ and (D).

The correction coefficients of the individual levels of resolution are multiplied (calibrated) with the calibration factors G1 ... G6 determined in this manner. Those coefficients which refer to the respectively to be corrected image point (the diagonal elements in the matrix representation), are of course not calibrated.

White Normalization and White Border Normalization:

The reflex and scattered light correction are followed by the white normalization and white border normalization in the above already described manner. Thereafter is carried out, as the last correction measure, a spectral or wavelength correction for the interference filters used for the spectral splitting.

Spectral Correction:

The spectral characteristics of interference filters are, as already mentioned above, dependent on the angle of incidence of the light beams. This angle is not constant, but dependent on the position of the measured image point on the measured object. However, it can be calculated from the position of the respective image point, and the filter characteristic actually in effect for the respective image point position can then be determined therefrom.

When the spectrum measured under a preselected angle of incidence of γ with the use of preselected interference filters is referred to as $(SP)_k$, a corrected spectrum $(SP)_k$ can be calculated therefrom for the nominal spectral ranges (for example, 400, 420, 440 ... 680, 700 nm) by a spline interpolation according to Formula 4:

$$(SP)_k = (IM)_k * (SP)_\gamma,$$

wherein $(IM)_\gamma$ is an interpolation matrix valid for the angle of incidence γ with $n^2$ elements when N is the number of the discreet spectral values (wavelength regions) of the spectrum. In the present example with 16 discreet spectral channels, the matrix includes 16*16=256 elements. The elements of the interpolation matrix $(IM)_\gamma$ can be determined in the known manner by test measurements.

The interpolation matrices (IM)γ associated with the spectral correction in accordance with the invention are now determined and stored for a number, for example 50, of discreet angles of incidence γ (for example between 0° and 17°). One of these 50 discreet angles of incidence γ is appointed to each image point region of, for example, 8*8 pixels according to its location on the measured object. Subsequently, the spectrum (SP)γ of each image point (previously of course contrast corrected) according to the preceding description is recalculated by way of the interpolation matrix $(IM)_\gamma$ belonging to the associated angle of incidence γ according to the above formula for the nominal spectral regions of, for example, 400, 420, 440 ... 680, 700 nm.

After this last correction measure, corrected image data (spectra) 72 are present for each image point of the measured object which are then available for further use or analysis.

Figure 10:
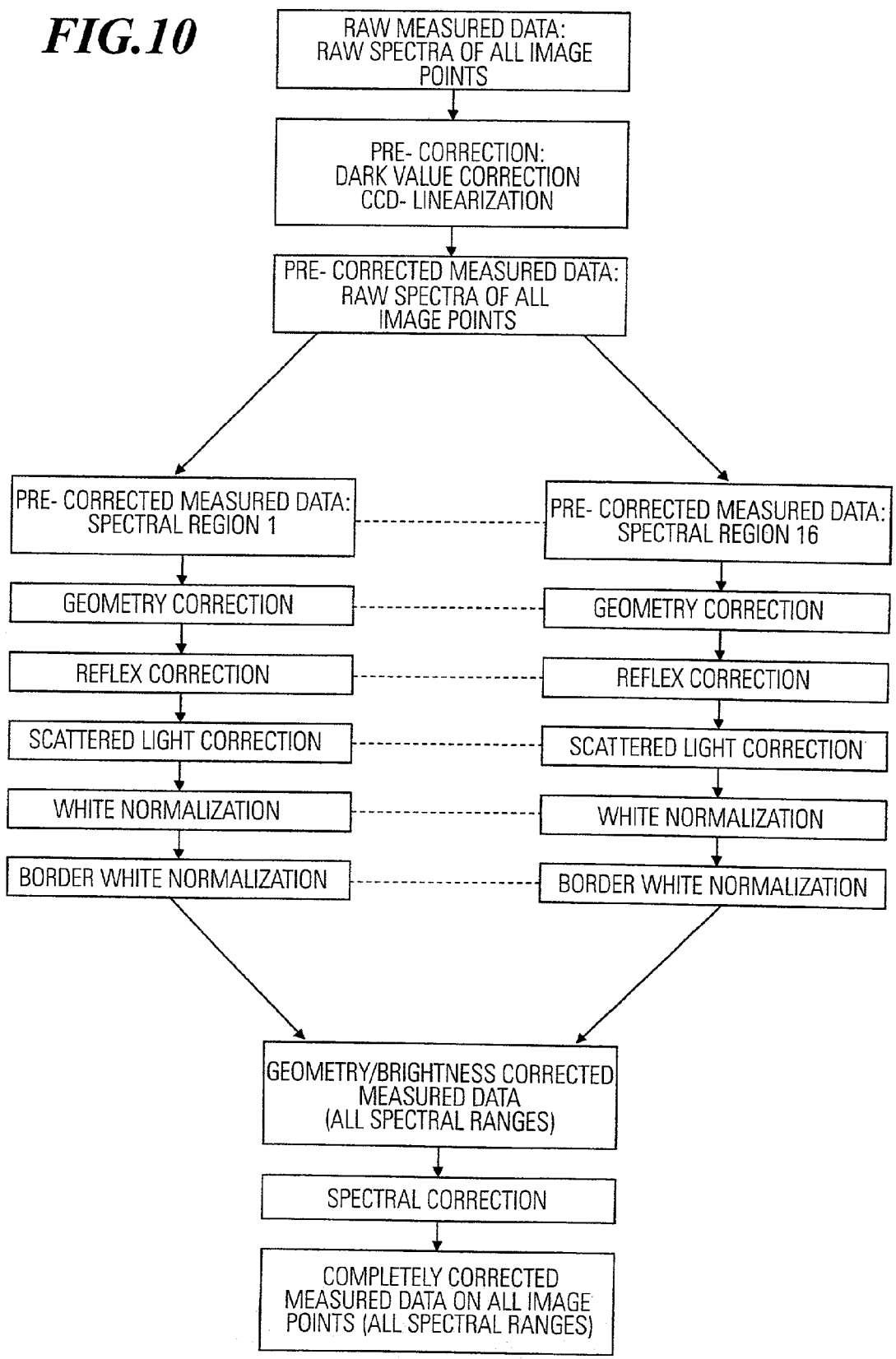
FIG. 10 is a schematic summary of all correction measures.

The precision of the corrected image data obtained in this manner is comparable with that of image data measured with conventional color measurement apparatus. The diverse correction measures are again clearly illustrated in summary in FIG. 10.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. Device for the pixel-by-pixel photoelectric measurement of a planar or flat measured object or object to be measured, comprising:
    illumination means for illuminating the measured object or object to be measured with at least one essentially parallel light bundle at an angle of incidence of essentially 45°+/−5°;
    a two-dimensional array of light converter elements for producing electric signals in response to light remitted by the measured object or object to be measured;
    a tele-centrical imaging optics for imaging each point of the measured object or object to be measured onto the light converter element array at essentially the same observation angle of essentially 0° and with the same aperture angle of essentially maximally 5°;
    imaging means for imaging the measured object or object to be measured onto the two-dimensional array of light converter elements;
    filters provided in the imaging light path for wavelength selective filtering of the measurement light impinging on the light converter elements;
    signal processing means for processing the electrical signals produced by the light converter elements and for converting them into corresponding digital raw measured data; and
    data processing means for processing of the raw measured data into image data representing the colours of the individual pixels of the measured object.

2. Device according to claim 1, wherein the illumination means include an illumination lens and a light source positioned in the focal point thereof.

3. Device according to claim 2, wherein the illumination means include intensity equalisation means for producing an even illumination strength over essentially the whole illuminated surface of the measured object or object to be measured.

4. Device according to claim 3, wherein the intensity equalisation means are formed by a blend filter.

5. Device according to claim 3, wherein the blend filter is colour neutral.

6. Device according to claim 2, wherein the illumination lens is a Fresnel lens.

7. Device according to claim 6, wherein the blend filter is positioned at or on the Fresnel lens.

8. Device according to claim 2, wherein the light source is a flash light source.

9. Device according to claim 1, wherein the device is a video camera and the tele-centrical imaging optics is formed by a two-dimensional image sensor of the camera having a two-dimensional converter element array, an imaging lens of the camera with an entry shutter, and a tele-lens of the camera positioned before the imaging lens, the focal point of the tele-lens being located in or close to the entry shutter.

10. Device according to claim 9, wherein the tele-lens is constructed as a Fresnel lens.

11. Device according to claim 10, wherein the video camera is a black and white camera and the filter means include a set of bandpass filters constructed as interference filters for the wavelength-selective filtering of the measuring light impinging on the light converter elements, and drive means for selectively moving the bandpass filters into the imaging light path.

12. Device according to claim 11, wherein the drive means are constructed for sequentially moving the bandpass filters into the imaging light path.

13. Device according to claim 11, wherein about 16 bandpass filters of about 20 nm bandwidth each are provided which essentially cover the spectral range of 400–700 nm.

14. Device according to claim 11, wherein the bandpass filters are sequentially mounted on a rotatable filter wheel.

15. Device according to claim 1, wherein the filter means for the wavelength-selective filtering of the measuring light impinging on the light converter elements are constructed as bandpass filters positioned directly onto the light converter elements.

16. Device according to claim 9, including several video cameras each with a two-dimensional image sensor and an imaging lens with an entry shutter, whereby each video camera is constructed for the measurement of a different wavelength range and the video cameras are positioned such that their entry shutter is located in or close to the focal point of the tele-lens.

17. Device according to claim 16, wherein each video camera is constructed for the measurement of a different wavelength range by the inclusion of upstream bandpass filters.

18. Device according to claim 9, including several two-dimensional image sensors and further comprising in the light path of the imaging optics a colour-selective beam splitter arrangement for directing respectively one spectral range of the measuring light onto one of the image sensors.

19. Device according to claim 18, wherein the colour-selective beam splitter arrangement splits the measuring light into about 16 spectral ranges of 20 nm bandwidth each, which essentially cover the spectral range of 400–700 nm.

20. Device according to claim 18, further comprising three semi-transparent mirrors for the splitting of the measuring light into four equal channels and three colour-selective beam splitters in each channel which divide the channel into four spectral ranges.

21. Device according to claim 20, further comprising bandpass filters of about 20 nm bandwidth each which are positioned after the colour-selective beam splitters and together essentially cover the spectral range of 400–700 nm.

22. Device according to claim 20, wherein the semi-transparent mirrors, the colour-selective beam splitters and the image sensors are positioned on the interfaces of laminated glass prisms.

23. Device according to claim 22, wherein the bandpass filters are also positioned on the interfaces of the laminated glass prisms.

24. Device according to claim 1, wherein the data processing means is constructed for carrying out a geometry correction for compensating the geometric distortions generated by the imaging means.

25. Device according to claim 24, wherein the data processing means include a correction table in which are stored for each image point the position deviations relative to a nominal position determined by way of a test image, and wherein the data processing means is constructed for correcting the position of each image point on the basis of the position deviations stored in the correction table.

26. Device according to claim 25, wherein in the correction table the same position deviations are respectively associated with a small region of adjacent image points.

27. Device according to claim 1, wherein the data processing means is constructed for carrying out a reflex correction for reducing reflection effects.

28. Device according to claim 27, wherein the data processing means is constructed for calculating a point-symmetrical reflection image from the measured data of the measured object and subtracting the same pixel-by-pixel form the measured data of the measured object.

29. Device according to claim 28, wherein the data processing means is constructed for carrying out the calculation of the reflection image at a lower resolution than that of the measured data.

30. Device according to claim 1, wherein the data processing means is constructed for carrying out a scattered light correction for reducing scattered light effects.

31. Device according to claim 30, wherein the data processing means is constructed for limiting the scattered light correction to selectable regions of the measured object.

32. Device according to claim 30, wherein the data processing means is constructed for calculating from the measured data of the measured object a scattered light image and subtracting the same pixel-by-pixel form the measured data of the measured object.

33. Device according to claim 32, wherein the data processing means is constructed for carrying out the calculation of the scattered light image at binary graduated resolutions, whereby for each image point a number of analysis regions of graduated resolution and surrounding the image point are selected, and beginning with the largest analysis region and the coarsest resolution the scattered light contribution of each analysis region to the inwardly next analysis region with the next finer resolution is calculated, and the scattered light contribution at the highest resolution is only calculated for the innermost analysis region.

34. Device according to claim 33, wherein the data processing means is constructed for calculating the scattered light contributions of the individual analysis regions by way of scattered light correction coefficients, whereby each level of resolution is associated with its own set of scattered light coefficients and the scattered light coefficients of each level of resolution describe those scattered light portions which are received by one image point of the respective level of resolution receives from the other image points of the same level of resolution.

35. Device according to claim 34, wherein the data processing means is constructed for calculating the scattered light contributions of the individual analysis regions by way of calibrated scattered light correction coefficients, whereby the sets of scattered light coefficients each associated with one level of resolution are weighted by a calibration factor and the calibration factors are selected such that a residual error remaining after the scattered light correction is minimal.

36. Device according to claim 1, wherein the data processing means is constructed for carrying out a white normalisation, whereby the measured data of the measured object are normalized to the brightness values of a white reference field.

37. Device according to claim 1, wherein the data processing means is constructed for carrying out a white border normalisation, whereby for each measurement the brightness of a white border region is determined and the measured data are normalized to the mean brightness of this border region.

38. Device according to claim 1, wherein the data processing means is constructed for carrying out a spectral correction for consideration of the spectral characteristic of interference filters depending on the angle of incidence of the light beams.

39. Device according to claim 38, wherein an interpolation matrix is stored in the data processing means respectively for a preselected number of angles of incidence, the data processing means are constructed for assigning a discrete angle of incidence to each image point on the basis of its relative location on the measured object, and for correcting the spectrum of the respective image point formed by the measured data, by way of the interpolation matrix respectively associated with the discrete angle of incidence.

* * * * *